United States Patent [19]

Bokros

[11] 4,300,244
[45] Nov. 17, 1981

[54] CARDIOVASCULAR GRAFTS
[75] Inventor: Jack C. Bokros, Alpine, Calif.
[73] Assignee: CarboMedics, Inc., San Diego, Calif.
[21] Appl. No.: 77,047
[22] Filed: Sep. 19, 1979
[51] Int. Cl.³ .............................. A61F 1/00; A61F 1/24
[52] U.S. Cl. ...................................... 3/1.4; 128/334 R
[58] Field of Search .................... 3/1, 1.4; 128/334 R, 128/334 C, 335, 335.5

[56] References Cited
U.S. PATENT DOCUMENTS

| | | | |
|---|---|---|---|
| 3,479,670 | 11/1969 | Medell | 128/334 R X |
| 3,677,795 | 7/1972 | Bokros et al. | 3/1.4 X |
| 3,993,078 | 11/1976 | Bergentz et al. | 3/1.4 X |
| 4,130,904 | 12/1978 | Whalen | 3/1.4 |
| 4,169,477 | 10/1979 | Bokros | 128/334 R |

FOREIGN PATENT DOCUMENTS 2001869 2/1979 United Kingdom .................... 3/1.4

*Primary Examiner*—S. Leon Bashore
*Assistant Examiner*—Ferris H. Lander
*Attorney, Agent, or Firm*—Fitch, Even, Tabin, Flannery & Welsh

[57] ABSTRACT

Springs are used to form cardiovascular grafts.

A tightly wound spring coated with carbon while in a stretched position will have a biocompatible interior surface which provides an unobstructed passageway for blood. Fabric sleeves may be employed around springs to improve the fluid integrity of the interior surfaces.

Springs may also be used to join blood vessel segments by puncturing one segment of the blood vessel with a first end of a spring, coiling the spring therearound, puncturing a second segment of the blood vessel with a second end of the spring and coiling the spring therearound.

13 Claims, 16 Drawing Figures

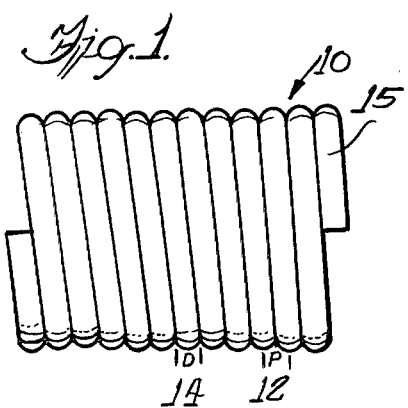
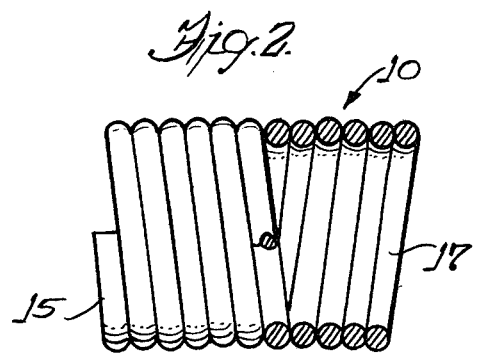
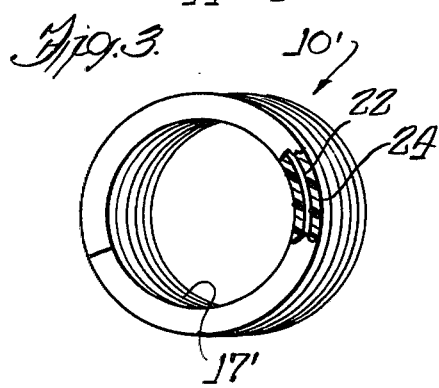
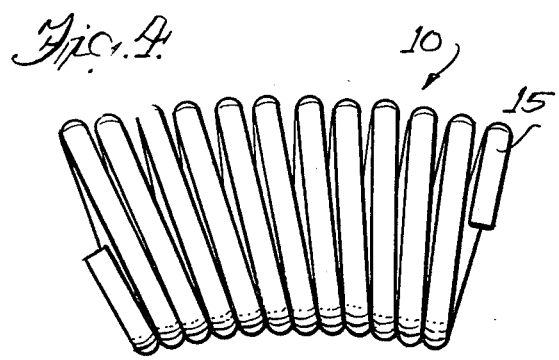
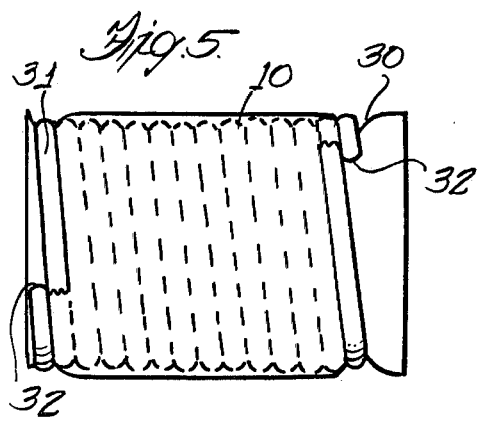
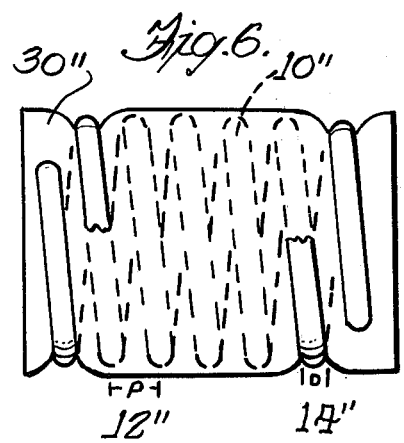
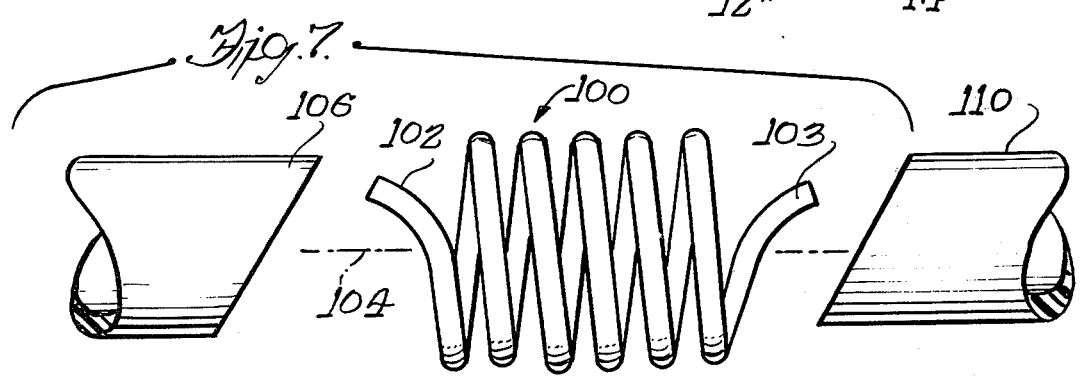

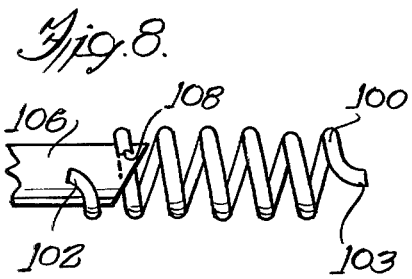
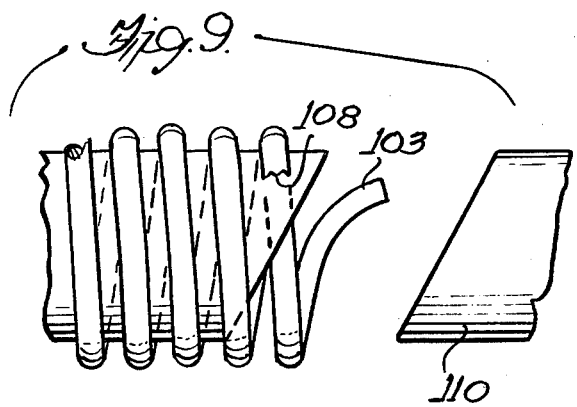
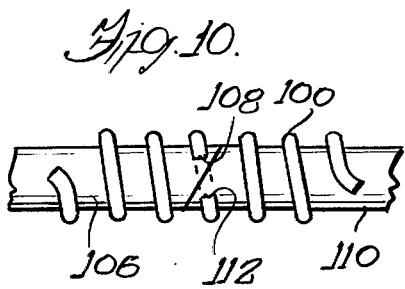
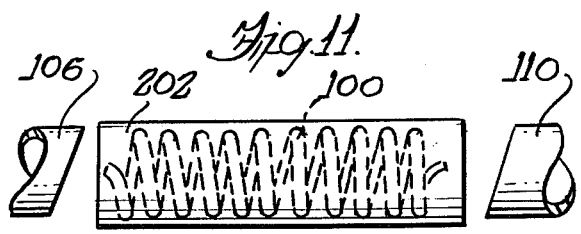
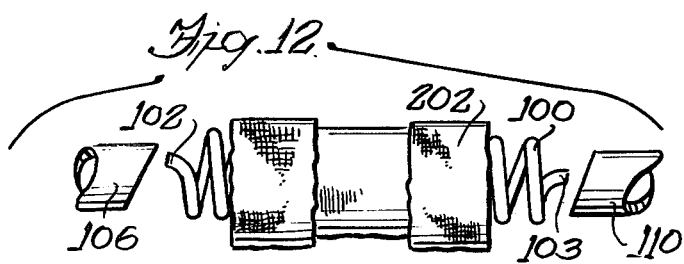
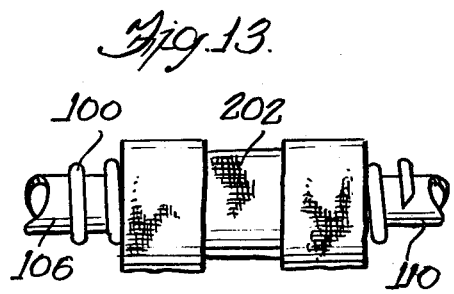
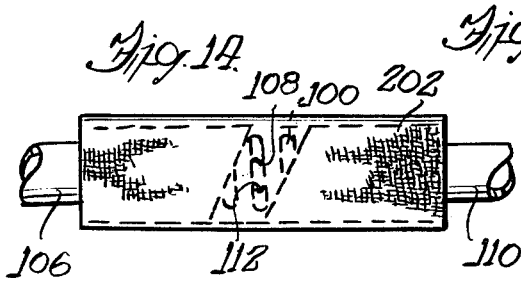
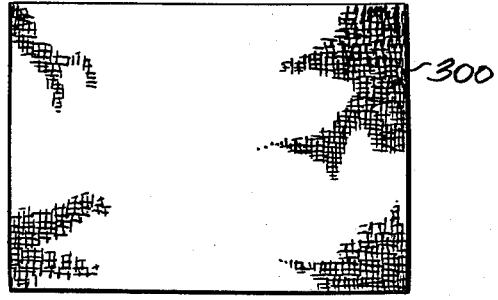
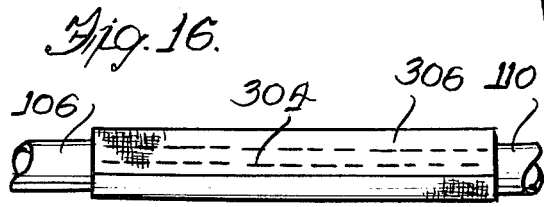
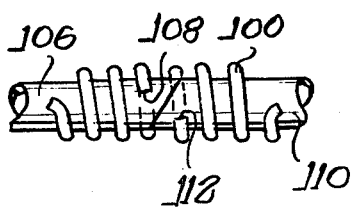

CARDIOVASCULAR GRAFTS

FIELD OF THE INVENTION

The present invention relates to prosthetic devices and, more particularly, to prosthetic devices designed as cardiovascular implants.

BACKGROUND OF THE INVENTION

Conventionally, vascular grafts with diameters greater than 6 millimeters, fabricated from a variety of synthetic materials, have been successfully used for a number of years in reconstructive surgery. The same degree of success has not been achieved with conventional grafts having diameters smaller than 6 millimeters.

Certain characteristics are recognized as necessary for artificial vascular grafts. The graft must have such physical properties that it can be readily handled and manipulated during the specific surgery calling for its use. It must be flexible as it is sometimes necessary in surgery to bend a graft around or under a body organ. A prosthesis will, of course, be required to flex within the human body in which it is implanted. While flexible, it must nonetheless have a certain rigidity so as to prevent collapse or kinking with subsequent closing of the passageway. The prosthesis should maintain its strength and flexibility permanently.

Additionally, a prosthesis should be non-toxic and acceptable to body tissues and fluids. A vascular graft in particular must be biocompatible to blood, and surfaces interfacing with blood must be thromboresistant. An effective prosthesis should also be porous, avoid the formation of fluid pockets, and promote the growth through the fabric of repair tissue.

Tubes of fabric have been found to be useful as cardiovascular grafts. Fabric tubes can be assured to be biocompatible with blood by coating the interior surface of the tube with carbon, as described in U.S. Pat. application Ser. No. 813,538, filed July 7, 1977, in the name of Jack C. Bokros, now U.S. Pat. No. 4,169,477.

A spring inserted inside a fabric tube adds strength to the tube and permits greater flexing without kinking.

An example of such a spring used to strengthen a fabric prosthesis is taught in U.S. Pat. No. 4,130,904 issued Dec. 26, 1978, to Robert L. Whalen, which shows a spring frictionally engaged between two concentric fabric tubes. The inside surface of the inner tube is designed so that a thin layer of blood will coagulate thereon thus coating the interior surface. Because of the configuration of concentric tubes, air pockets exist between the fabric tubes into which blood can seep and therein coagulate. It is the property of blood that coagulated blood can hasten further coagulation of blood and, therefore, a prosthesis which relies on blood coagulation to form a biologically integrated surface may lead eventually to sufficient buildup of coagulated blood to hinder blood flow. It would therefore be desirable to have a surface which is biocompatible without relying on coagulation and which eliminates pockets in which clots can begin. To this end the use of springs is taught in the instant invention which are in themselves biocompatible and thromboresistant and which either in themselves or in conjunction with a single biocompatible and thromboresistant layer of fabric join segments of blood vessels.

Accordingly, it is an object of this invention to provide strong flexible and durable cardiovascular prostheses which will not kink or collapse through the use of springs which are biocompatible and thromboresistant.

It is a further object of this invention to provide improved blood compatible surfaces for vascular grafts in which the surfaces are well washed by flowing blood so as to prevent blood clotting.

BRIEF DESCRIPTION OF THE INVENTION

Generally, the present invention provides flexible, biologically compatible cardiovascular prostheses suitable for prolonged or permanent use in a living body, such as for tubular grafts to replace veins or arteries in the cardiovascular system or to join severed ends of such veins or arteries together.

The cardiovascular prostheses are made from springs which provide the strength and flexibility required and also may be coated so as to have a surface with excellent biocompatible properties.

A tightly wound spring provides an interior passageway whose surface may be coated with carbon for biocompatibility. When springs are bent, the coils separate. Therefore, the cardiovascular graft may include a tubular fabric array as a sleeve around the spring.

Springs may also be used to join severed blood vessels where suturing the ends together would be difficult because of the small size of the blood vessels. The springs so employed have one end which is inserted first through a first segment of the blood vessel and coiled therearound and have a second end which is inserted through a second blood vessel segment and coiled therearound. Thereafter a fabric array may optionally be employed to seal the junction of the blood vessel segments.

BRIEF DESCRIPTION OF THE DRAWINGS

FIG. 1 is an elevation view of the helical spring for use as the cardiovascular graft.

FIG. 2 is a spring used as the cardiovascular graft partially cut away;

FIG. 3 is an end view, partially in cross-section, of a polymer coated metal coil;

FIG. 4 is a tightly wound spring in a flexed position;

FIG. 5 is a spring used as a cardiovascular graft ensleeved in a tubular fabric array;

FIG. 6 is a cardiovascular graft employing a spring where a pitch is considerably greater than the diameter of the wire and is ensleeved in a tubular fabric array;

FIG. 7 is an elevation view of a spring which is used to join two severed ends of a blood vessel;

FIG. 8 is an elevation view of a spring which has punctured a severed end of a blood vessel and is partially coiled around the blood vessel;

FIG. 9 is an elevation view of a spring coiled through and around a blood vessel, exposing only an end for inserting into a second segment of a blood vessel;

FIG. 10 is an elevation view of a blood vessel in which two severed segments have been sutured together by use of a spring which has punctured each end and been coiled around each segment of the blood vessel;

FIG. 11 illustrates a vascular prosthesis including a spring and a fabric array which is used to join two severed segments of a blood vessel by puncturing the ends of the blood vessel with the spring and coiling the spring around the ends of the blood vessel;

FIG. 12 is an elevation view of the prosthesis shown in FIG. 11 where the ends of the fabric array have been cuffed back exposing coils of the spring;

FIG. 13 is an elevation view of the prosthesis shown in FIG. 11 with the fabric array cuffed back and the spring having punctured each segment of the blood vessel and having been coiled around each segment of the blood vessel;

FIG. 14 is an elevation view of a severed blood vessel joined by the prosthesis shown in FIG. 11;

FIG. 15 is an organopolymer array of fabric which is to be wrapped around a blood vessel having been joined together as in FIG. 10.

FIG. 16 is a blood vessel which has been joined as in FIG. 10 having been wrapped by a fabric array as shown in FIG. 15 and sutured along the overlapping portions to form a tubular array of fabric around the junction.

FIG. 1 illustrates a helical spring 10 which serves as a cardiovascular graft. The spring 10 is formed so that the pitch P 12 being the distance between the center of one coil and the center of an adjacent coil as measured along a line parallel to the axis of the spring is equal to the dimension D 14 of the spring wire 15 as measured along the same axis. Of course for a spring made of round wire, the dimension D 14 will be equal to the diameter of the spring wire. The tightly wound spring will have a convoluted interior surface 17 providing a passageway for blood. The interior surface 17 being made from smooth wire 15 will provide a passageway for blood which is both unobstructed and easily washed by blood.

A tightly wound spring where the pitch 12 is equal to the diameter 14 of the wire 15 has coils in contact with each other inhibiting seepage between the coils. The spring has a natural biasing force holding the coils in surface-to-surface contact. The springs are coated with carbon so that the coating on each coil is in surface contact with the coating on adjacent coils. A spring 10' as shown in FIG. 3 may be composed of a metal wire 22 having an outer layer of some soft polymer 24 such as silicone rubber. Soft polymer coatings on the coils are squeezed together by the biasing force of the spring thereby improving the fluid integrity of the interior surface 17'. Seepage between the coils is lessened when the tightly wound wire spring is coated with polymer while in a stretched position by adding thickness to the coils preventing them from returning to their original position.

A metal spring or a spring coated with a flexible polymer coating may be further coated with a polymer such as expanded polytetrafluoroethylene which has a porous or fibrous surface. Expanded polytetrafluoroethylene such as that sold under the tradename "GORE-TEX" when coated with carbon has especially good blood compatible characteristics. The compliant porous or textured surface further enhances the self-sealing qualities of the cardiovascular graft.

The use of a porous or fibrous coating of polytetrafluoroethylene requires the use of a metal spring with a high modulous of elasticity to control the overall deformation of the device and prevent cracking of the coating.

When a tightly wound spring 10 is bent as shown in FIG. 4 the coils separate and the fluid integrity of the interior surface 17 is destroyed. Therefore, in most applications, a sleeve 30 comprised of a fabric array is provided as shown in FIG. 5. The fabric sleeve 30 has an interior diameter generally equal to the exterior diameter of the spring 10 so as to frictionally engage with the spring. It may be desirable, however, that the outside diameter of the spring 10 be slightly larger to require some stretching of the fabric sleeve 30 so that the spring 10 is held securely in place.

To further hold the spring 10 in place securely relative to the sleeve 30, the spring 10 is poked through the fabric as shown in FIG. 5 and at least one coil 31 of the spring is wound therearound. The ends of the springs 32 may be blunted or may be secured to the next coil so that a protruding end does not cause irritation to surrounding tissue. The ends of the fabric can be sutured to a vessel in the usual way.

In an alternative embodiment, as shown in FIG. 6, a loosely wound spring 10" may be disposed in a fabric sleeve 30". To create an interior surface with improved blood flow characteristics and biocompatibility the dimension 14" of the wire as measured parallel to the helical axis should be no less than one half the pitch P 12" of the spring 10".

Such springs may be made from a biologically inert metal such as titanium, molybdenum, tantalum, stainless steel or a cobalt based alloy such as MP35N. The springs are coated with carbon, and although only the carbon coating will come into contact with blood, metals which are to be implanted in a human body should be biocompatible and corrosion resistant so as not to weaken the spring or induce clotting. The carbon coating may be applied to a metal or polymer or polymer coated metal as described in U.S. Pat. No. 3,952,334 issued to Bokros, et al. on Apr. 27, 1976. In a tightly wound spring, the spring is stretched during the coating process to insure adequate coating on all surfaces of the spring.

In order that the coating not crack as the spring is flexed, the carbon is isotropic with a B.A.F. of 1.3 or less, has a modulus of elasticity of between $2 \times 10^6$ psi and $5 \times 10^6$ psi, a density of at least 1.5 gm/cc and a thickness of no greater than 1.0 micron.

The choice of material for the spring 10, or size, and the strength of the wire will depend on the particular use for the prosthesis. The coils comprising the spring 10 should be strong enough so as not to collapse under the pressure to which they will be subjected. The coils should have sufficient elasticity to endure both the bending necessary for implantation during surgery and for the flexing which may take place once they are implanted in the body. They should also rebound from such flexing without deformation or kinking. The tubular fabric array may be formed of non-woven fabric structures such as porous polytetrafluoroethylene sold under the trade name "GORE-TEX", or may be structured from woven, knitted, or felted organopolymeric fiber. In a woven or knit fabric array, the organopolymeric fibers which are relatively small in diameter are able to sustain the functional stresses intended for the prosthetic fabric and provide for a higher degree of flexibility without straining more than about 5 percent. Fibers should generally have a major diameter dimension of less than about 25 microns and a minor diameter dimension of at least 5 microns, although fibers as small as 1 micron might be used in certain applications. By major diameter dimension is meant the widest dimension of the fiber in direction orthogonal to the longitudinal axis of the fiber, and by minor diameter dimension is meant the narrowest dimension of the fiber in a direction orthogonal the longitudinal axis of the fiber. Of course, for a fiber of circular cross section the major and minor dimensions will be the same, but it should be appreciated that the invention does contemplate fibers of non-circular cross section. However, deviations from circular fiber cross sections generally lead to stiffer fabrics because of the increased interfibral friction, and increased force is required for bending and unbending of the fiber filaments.

Tubular knit fabric arrays are particularly preferred fabric structures, and in this regard the term "knit" is used generally to include weft knit and warp knit fabric arrays. Weft knit fabric structures (including double knit structures) utilize interlocked loops in filling-wise of weft direction where warp knit structures utilize fabric loops interlocked in a lengthwise, or warp direction. Weft knit fabrics generally have two dimensional elasticity or stretch where warp fabrics generally have unidirectional (width-wise) elasticity. The different elasticity properties of the various knit or woven structures may be beneficially adapted to the functional requirement of the particular prosthetic application.

The interior of the tubular fabric sleeve 30 must be biocompatible with blood. The best mode for achieving this biocompatibility is to coat the interior surface of the fabric sleeve 30 with carbon, using a method such as that described in application Ser. No. 813,538 filed July 7, 1977, in the name of Jack C. Bokros, et al., now U.S. Pat. No. 4,169,477. Suitable fabrics for coating include polyethylene terepthalate polytetrafluoroethylene and dacron.

The carbon coating should be at least about 0.1 micron thick, should be adherent and, in order to provide a high tensile strength, should have a BAF (Bacon Anistropy Factor) of about 1.3 or less and preferably about 1.2 or less. Generally, a coating thickness of about 1000 to 7000 Å i.e., 0.1 to 0.7 microns, and preferably about 3000 to about 5000 Å of intermediate density of carbon, i.e., about 1.6 to 2.0 grams per cubic centimeters, is employed. Greater thicknesses may crack and flake. Preferably the vapordeposited carbon has a density of about 1.8 grams per cubic centimeter. Such vapor-deposited carbon exhibits biocompatible properties and excellent adhesion to small organopolymeric fibers. As a result, the coated fabrics exhibit excellent properties for use as a prosthetic fabric device and are considered to be acceptable for implantation within the human body.

The prosthesis can be joined at each end to a cardiovascular segment by suturing or may be fitted to a rigid fitting which is secured in an appropriate manner to the patient.

Blood vessels under 2 millimeters in diameter present special problems in that suturing is difficult making the use of a prosthesis as described above difficult. A method therefore has been devised which employs a spring to join two segments of a severed blood vessel together.

In a spring 100 as shown in FIG. 7 two ends 102 and 103 are bent away from the axis 104 of the helix. The spring 100 should be a minimum of four and preferably at least six coils. The spring 100 should be loosely wound. The first segment of the blood vessel 106 is punctured from inside at a point 108 near the severed end of the first segment of the blood vessel 106 by the first terminus 102 of the spring 100. The spring 100 is rewound around the first segment of the blood vessel 106 as shown in FIG. 8 in a first direction which coils the spring 100 around the first segment of the blood vessel 106. This coiling is continued until almost the entire spring 100 is coiled around the first segment of the blood vessel 106. The second terminus of the spring 103 and perhaps one or two coils should not be passed through the puncture point 108. The exposed second terminus of the spring 103 as shown in FIG. 9 is then positioned for insertion into the second segment of the blood vessel 110. The second terminus of the spring 103 punctures the second segment of the blood vessel 110 at a point 112, and the spring 100 is turned in a second direction opposite the first direction so that a plurality of coils coil the second segment 110 of the blood vessel. This turning is done until at least two coils and preferably three up to one-half the total number of coils of the spring 100 are wound around the second segment of the blood vessel 110. The two segments of the blood vessel 106 and 110 are thereby joined as shown in FIG. 10.

In joining the two segments 106 and 110 of a blood vessel simply by use of a spring 100, it is necessary that the segments 106 and 110 of the blood vessel be punctured at points 108 and 112 sufficiently far from the severed ends of the segments 106 and 110 so that a good junction is formed between the segments 106 and 110 to insure good fluid sealing and to allow for good tissue healing. The use of the spring to join sections of a first segment 106 to a second segment 110 by a spring 100, as shown in FIGS. 7 through 10 might by itself accomplish an effective seal between the two segments. However, if additional sealing of the junction between the two segments 106 and 110 is required, it may be advantageous to use a tubular array of fabric 202 in conjunction with the spring 100 to create an effective seal between the segments 106 and 110 of the blood vessel.

A fabric array 202 as shown in FIG. 11 disposed around the spring 100 may be cuffed back as illustrated in FIG. 12 on both ends exposing a plurality of coils on each end of the springs 100. As described previously, and illustrated in FIG. 13, a first terminus 102 of the spring may be inserted from the inside to the outside of an end 106 of a severed blood vessel. The spring 100 is then coiled around the first segment of the blood vessel 106 at least four and preferably at least six times. The second terminus 103 then punctures the second segment of the blood vessel 110 and is coiled around so that at least two and preferably three or more coils encircle each end of the blood vessel. The fabric array 202 is then uncuffed forming a union between the ends 106 and 110 of the blood vessel as illustrated in FIG. 14. The use of a spring 100 with a fabric array 202 provides a better seal at the junction of the ends of the segments 106 and 110 of the blood vessel. A spring 100 ensleeved in a fabric array 202 can also be used as a section to join blood vessel segments when some distance separates two segments of a blood vessel.

The junction of two segments of a blood vessel which have been joined by means of a spring 100 as described above may alternatively be sealed with the use of a flat piece of fabric array 300 which has been made biocompatible preferably by carbon coating as above-described. The fabric array 300 is wrapped around the junction until a portion 302 thereof overlaps itself. The overlapping sections are then sutured together with sutures 304 resulting in a tubular seal 306 as illustrated in FIG. 16.

Although the invention has been described with regard to certain preferred embodiments, it should be understood that the scope of the invention is defined in the appended claims.

Various of the features of the invention are set forth in the following claims.

What is claimed is:

1. A vascular prosthesis for implantation in a living body comprising:
   a tubular configuration of organopolymeric fabric;
   dense, isotropic carbon coating along at least the interior surface of said tubular configuration; and
   a biocompatible wire in the form of a helical spring of uniform spring diameter disposed inside said tubular configuration and having an outside spring diameter such that said spring is in surface contact with said carbon coated interior of said tubular configuration;
   said spring having a pitch not greater than twice the diameter of said wire;
   whereby a blood compatible surface is defined on the interior of said prosthesis where said blood compatible surface consists of at least 50% exposed surface of said spring and the remainder of said blood compatible surface consists of portions of said interior surface of said tubular configuration.

2. A vascular prosthesis according to claim 1 in which a generally cylindrical passageway is provided for blood which is free from obstruction so that blood interfaces with said prosthesis only at said blood compatible surface.

3. A cardiovascular prosthesis according to claim 1 where said wire is metal.

4. A cardiovascular prosthesis according to claim 1 wherein said wire is polymer.

5. A cardiovascular prosthesis according to claim 1 where said wire comprises a metal core surrounded by a polymer coating.

6. A cardiovascular prosthesis according to claim 1 where said carbon coating on said organopolymeric fabric has a thickness of between about 0.1 and about 0.7 microns a B.A.F. of about 1.3 or less and a density of between about 1.6 gm/cc and about 2.0 gm/cc.

7. A cardiovascular graft according to claim 1 where the pitch of said spring is equal to the diameter of said wire.

8. A vascular prosthesis according to claim 1 wherein said fabric is an array of fibers.

9. A vascular prosthesis according to claim 1 wherein said fabric is a porous polymeric material.

10. A method for grafting a first segment with a second segment of a small blood vessel comprising:
    cuffing back a first and a second end of a tubular configuration of organopolymeric fabric and dense isotropic carbon coating along an interior surface of said tubular configuration, where said tubular configuration is disposed around a helical spring which is biocompatible with blood and vascular tissue and which has a first terminus and a second terminus bent outward from an axis of said helix,
    puncturing the first segment of the blood vessel with said first terminus from the inside to the outside of the blood vessel,
    rotating said spring about its axis in a first direction a plurality of turns thereby winding said spring around the first segment of the blood vessel;
    puncturing the second segment with said second terminus from the inside to the outside of the blood vessel;
    rotating said spring around its axis in a second direction a plurality of turns thereby winding said spring around the second segment until severed coils are wound around the second segment while several coils remain wound around the first segment; and
    uncuffing said tubular configuration so that said tubular configuration extends over the junctions of said spring and the first and second segments whereby the first segment and the second segment are joined together to form a unitary blood conduit.

11. A method for grafting a first segment with a second segment of a small blood vessel according to claim 10 where said spring is coated with carbon.

12. A method according to claim 10 wherein said tubular configuration is an array of fibers.

13. A method according to claim 10 wherein said tubular configuration is formed from a porous polymeric material.

* * * * *